United States Patent [19]

Nudelman et al.

[11] 4,180,660

[45] Dec. 25, 1979

[54] CEPHALOSPORIN DERIVATIVES

[75] Inventors: Abraham Nudelman, Rehovot; Abraham Patchornik, Ness Ziona, both of Israel

[73] Assignee: Yeda Research and Development Co. Ltd., Rehovot, Israel

[21] Appl. No.: 938,844

[22] Filed: Sep. 1, 1978

Related U.S. Application Data

[62] Division of Ser. No. 839,165, Oct. 4, 1977, Pat. No. 4,122,260.

[51] Int. Cl.² ............................................. C07D 501/20

[52] U.S. Cl. ....................................... 544/28; 544/21; 424/246

[58] Field of Search .............................. 544/28, 30, 21

[56] References Cited

U.S. PATENT DOCUMENTS 3,252,973  5/1966  Flynn ..................................... 544/28

Primary Examiner—Nicholas S. Rizzo
Attorney, Agent, or Firm—Stephen L. Nesbitt; L. Ruth Hattan; Eugene O. Retter

[57] ABSTRACT

New cephalosporin derivatives containing a formyl substituted pyrrole group and the processes for preparing same are described.

12 Claims, No Drawings

CEPHALOSPORIN DERIVATIVES

This is a division of application Ser. No. 839,165, filed Oct. 4, 1977, now U.S. Pat. No. 4,122,260.

BACKGROUND

1. Field of Invention

This invention is directed to novel cephalosporin derivatives which contain a formyl substituted 1-pyrryl acetyl group.

2. Prior Art

Compounds of the formula

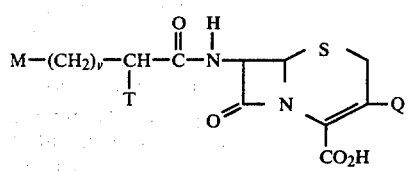

where M is N-pyrryl, T is hydrogen, v is O and Q is acetyloxymethyl have been described and claimed in U.S. Pat. No. 3,218,318 (assigned to Eli Lilly). The following patents, all assigned to Eli Lilly, disclose N-pyrryl derivatives of cephalosporins and/or penicillins. These patents include U.S. Pat. No. 3,351,596; U.S. Pat. No. 3,459,746; U.S. Pat. No. 3,728,342; U.S. Pat. No. 3,799,924; U.S. Pat. No. 3,252,973; U.S. Pat. No. 3,536,698; E. Germany No. 109,638 and W. German Offen. No. 2,262,477. Nowhere is it disclosed or suggested that the N-pyrryl group may be substituted with a formyl group.

Belgium Pat. No. 768,653 to Ciba-Geigy discloses compounds wherein M may be a wide variety of heterocyclic compounds which contain N, O and/or S and Q is $CH_2OH$ or CHO and T is hydrogen. Optionally M may be substituted with a formyl group although no formyl substituted M groups are described.

The compounds of the instant invention have not heretofore been suggested, described or claimed either in the Eli Lilly patents or in the Ciba-Geigy patent.

SUMMARY OF THE INVENTION

Compounds of formula 1 are useful as antibiotics

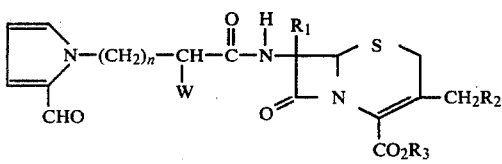

wherein n is 0, 1, 2 or 3; W is hydrogen, a straight or branched alkyl group of from 1 to 4 carbon atoms, a sulfonic acid group, or a $-(CH_2)_p-CO_2R_4$ group wherein p has a value of 0 or an integer of from 1 to 10 and $R_4$ is H, a pharmaceutically acceptable non-toxic cation selected from the alkali metal or the alkaline earth metal groups, ammonium, organic ammonium compounds or a straight or branched alkyl group of from 1 to 4 carbon atoms. $R_1$ is hydrogen or methoxy. $R_2$ is hydrogen, alkanoyloxy in which the alkanoyl group contains from 2 to 5 carbon atoms, 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1,2,3-triazol-5-ylthio or 1-methyl-1,2,3-triazol-5-ylthio; $R_3$ is hydrogen, a pharmaceutically acceptable non-toxic cation selected from the alkali metal or alkaline earth metal groups, ammonium or organic ammonium compounds; a straight or branched alkyl group of from 1 to 4 carbon atoms, an alkanoyloxymethyl group in which the alkanoyl portion is straight or branched and has from 2 to 5 carbon atoms, an alkanoylaminomethyl group in which the alkanoyl portion is straight or branched and has from 2 to 5 carbon atoms and the amine nitrogen may be substituted with a straight or branched alkyl group having 1 to 4 carbon atoms, an alkoxycarbonylaminomethyl group in which the alkoxy portion is straight or branched and has from 1 to 4 carbon atoms and the amine nitrogen may be substituted with a straight or branched alkyl group of from 1 to 4 carbon atoms, p-(alkanoyloxy)benzyl groups in which the alkanoyl portion is straight or branched and has from 2 to 5 carbon atoms, an aminoalkanoyloxymethyl group in which the alkanoyl portion has from 2 to 15 carbon atoms and the amino nitrogen may be mono- or di-substituted with a straight or branched alkyl group having from 1 to 4 carbon atoms; with the proviso that when $R_3$ is other than hydrogen or a cation and W is $-(CH_2)_p-CO_2R_4$ with p being from 1 to 10, then $R_4$ is other than hydrogen or a cation; and pharmaceutically acceptable salts thereof.

DETAILED DESCRIPTION

In formula 1 $R_3$ is in addition to hydrogen or a pharmaceutically acceptable cation a straight or branched alkyl group of from 1 to 4 carbon atoms or $R_3$ is represented by the structure

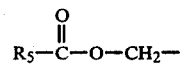

wherein $R_5$ is a straight or branched alkyl group of from 1 to 4 carbon atoms. $R_3$ is represented by the structure

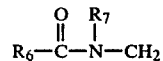

wherein $R_6$ is a straight or branched alkyl group of from 1 to 4 carbon atoms or a straight or branched alkoxy group of from 1 to 4 carbon atoms and $R_7$ is hydrogen or a straight or branched alkyl group of from 1 to 4 carbon atoms. $R_3$ is represented by the structure

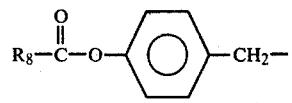

wherein $R_8$ is a straight or branched alkyl group of from 1 to 4 carbon atoms; and $R_3$ is represented by the structure

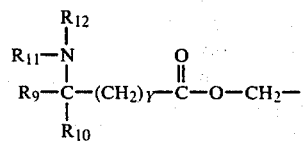

wherein Y is 0 or an integer of from 1 to 5, $R_9$ and $R_{10}$ are selected from hydrogen and a straight or branched alkyl group of from 1 to 4 carbon atoms and each of $R_{11}$ and $R_{12}$ is selected from hydrogen and a straight or branched alkyl group. $R_3$ represents hydrogen or a pharmaceutically acceptable non-toxic cation selected from an alkali metal or an alkaline earth metal ion such as sodium, potassium, magnesium or calcium. Additionally $R_3$ may also represent ammonium or an organic ammonium ion derived from primary, secondary or tertiary amines such as cyclohexyl-, diethyl- or trioctyl-amine.

Illustrative of the straight or branched 1 to 4 carbon alkyl groups which $R_5$ to $R_{12}$ may represent are the following: methyl, ethyl, propyl, iso-propyl, n-butyl, iso-butyl and tert-butyl.

$R_2$ is hydrogen or an alkanoyloxy group in which the alkanoyl moiety is straight or branched and has from 2 to 5 carbon atoms. Illustrative examples of the alkanoyl moiety are acetyl, propionyl and isobutyryl.

Additionally, $R_2$ is 1,3,4-thiadiazol-2-ylthio, 5-methyl-1,3,4-thiadiazol-2-ylthio, tetrazol-5-ylthio, 1-methyl-tetrazol-5-ylthio, 1,3,4-oxadiozol-2-ylthio, 5-methyl-1,3,4-oxadiozol-2-ylthio, 1-methyl-1,2,3-triazol-5-ylthio, 1,2,3-triazol-5-ylthio, the respective structures are shown below.

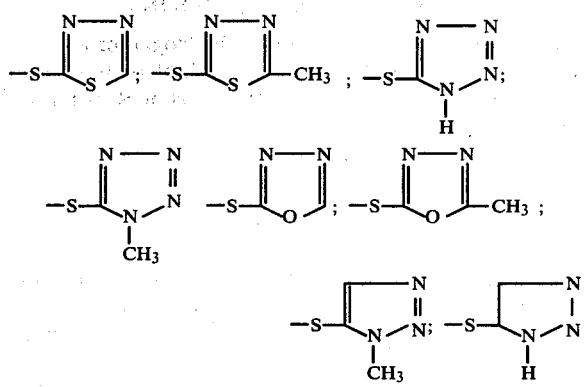

In formula 1, $R_1$ is hydrogen or methoxy. It is obvious that $R_1$ may occupy a position cis or trans to the substituent at position 6. The compounds in which $R_1$ is cis to the 6-position substituent are preferred.

In formula 1, n is 0, 1, 2 or 3. W, in formula 1, represents hydrogen, a straight or branched alkyl group of from 1 to 5 carbon atoms, a —$SO_3H$ group or a —$(CH_2)_p$-$CO_2R_4$ group wherein $R_4$ is hydrogen, a non-toxic pharmaceutically acceptable cation selected from an alkali metal, an alkaline earth metal, an ammonium ion, an organic ammonium ion, derived from a primary, a secondary or a tertiary amine such as, methylamine, dibutylamine or pyridine. Additionally, $R_4$ represents a straight or branched alkyl group of from 1 to 4 carbon atoms or an alkanoyloxymethyl group in which the alkanoyl moiety is straight or branched and has from 2 to 5 carbon atoms.

The non-toxic pharmaceutically acceptable inorganic acid addition salts of compounds of this invention such as mineral acid addition salts, for example, hydrogen chloride, hydrogen bromide, hydrogen iodide, sulfates, sulfamate, phosphate, and organic acid addition salts, for example, maleate, acetate, citrate, oxalate, succinate, benzoate, tartrate, fumarate, malate, mandalate, and ascorbate, are also included within the scope of this invention.

Also within the scope of this invention are the non-toxic pharmaceutically acceptable salts of the compounds of formula 1 of this invention wherein W represents —$(CH_2)_p$—COOH wherein p is 0 or an integer of from 1 to 10 or $SO_3H$ and compounds wherein $R_3$ represents hydrogen. Illustrative pharmaceutically acceptable salts of these acid derivatives are primary, secondary, or tertiary amines, for example, cyclohexylamine, diethylamine, and pyridine and alkali metal and alkaline earth metal cations, such as, sodium, potassium, magnesium and calcium.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds and mammals, for example, cats, dogs, cows, sheep and horses, and humans. For oral administration, the compounds may be administered in the form of tablets, capsules or pills in the form of elixirs or suspensions. For parenteral administration, they may be used in the form of a sterile aqueous solution which may contain other solutes, for example, enough saline or glucose to make the solution isotonic. For topical administration, the compounds may be incorporated in creams or ointments.

Illustrative examples of bacteria against which the compounds of this invention are active are *Staphylococcus aureus, Salmonella schottmuelleri, Klebsiella pneumoniae, Diplococcus pneumoniae,* and *Streptococcus pyrogenes.*

The individual optical isomers and mixtures thereof of the compounds of this invention when W is other than hydrogen and —$CO_2H$ are included within the scope of the invention.

An illustrative example of a cephalosporin derivative of this invention is 3-[(acetyloxy)methyl]-7-[[(2-formyl-1-pyrryl)acetyl]amino]-8-oxo-5-thia-1-azabicyclo-[4.2.0]oct-2-ene-2-carboxylic acid.

The compounds of this invention as represented by formula 1 are prepared by coupling compounds represented by formula 2

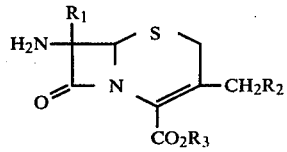

Formula 2 wherein $R_1$, $R_2$ and $R_3$ have the meanings defined for formula 1 with compounds of formula 3

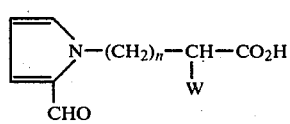

Formula 3 wherein n and W have the meanings defined for formula 1 and functional equivalents thereof in a suitable solvent.

Functional equivalents of the acids as represented by formula 3 include the acid halide, for example, the acid chloride, acid anhydrides, including mixed anhydrides with, for example, alkylphosphoric acid, lower aliphatic monoesters of carbonic acid or alkyl or aryl sulfonic acids.

When W is a —$(CH_2)_p$—$CO_2R_4$ group in compounds represented by formula 3 and p is from 1 to 10 then $R_4$ is other than hydrogen or a cation and when p is O, $R_4$ is as defined in formula 1 when said compounds are coupled with compounds of formula 2 to give compounds represented by formula 1. Additionally, a coupling agent such as N-ethoxycarbonyl-2-ethoxy-1,2-dihydroquinoline may be used and then W is other than —$SO_3H$ and $R_3$ and $R_4$ are other than hydrogen or a cation.

The coupling reaction is generally carried out in the presence of a solvent. Suitable solvents include ethyl acetate, acetone, dioxane, acetonitrile, chloroform, ethylene chloride, tetrahydrofuran dimethylformamide, ethanol, ethanol-benzene and benzene. As hydrophilic solvents are employed, mixtures of these solvents with water are also suitable for the above reactions. The coupling reaction is generally carried out in the presence of a base, for example, triethylamine or an alkaline bicarbonate. The temperature of the reaction may vary from −10° to 100° C., and the reaction time may vary from about ½ hour to 10 hours. The cephalosporin products are isolated by conventional methods.

Illustratively, coupling of compounds of formula 2 with compounds of formula 3 to give compounds as represented by formula 1 is accomplished using the general method of Spencer, et al., *J. Med. Chem.*, 9, 746 (1966). The acid to be coupled, compounds of formula 3, is reacted with an alkyl chloroformate, for example, isobutyl chloroformate, at about −10° C. in a solvent which contains an acid acceptor such as an alkaline bicarbonate. The amine, compounds as represented by formula 2, which is to be coupled to the acid is added and the temperature of the mixture is increased from about −10° C. to about 20° C. The reaction is completed and the coupled product is recovered by conventional means.

The acid, as represented by compounds of formula 3, is coupled to amine compounds as represented by compounds of formula 2 in a suitable solvent to give compounds represented by formula 1 using a carbodiimide, for example, N,N′-diisopropylcarbodiimide or N,N′-dicyclohexylcarbodiimide as taught by the general procedure in U.S. Pat. No. 3,252,973.

Illustratively, acids as represented by compounds of formula 3, W is other than —$SO_3H$ and $R_4$ is other than hydrogen or a cation, may be coupled with compounds of formula 2 using N-ethoxy-carbonyl-2-ethoxy-1,2-dihydroquinoline (EEDQ) with the proviso that $R_3$ is other than hydrogen or a non-toxic pharmaceutically acceptable cation. In the general method of Belleau, et al., *J. Am. Chem. Soc.*, 90, 1651 (1968), equivalent amounts of acid, amine and EEDQ are stirred in a suitable solvent for 6 to 10 hours at room temperature. The coupled product is then recovered by conventional techniques.

The acid as represented by formula 3 wherein n is 0 and W is —$SO_3H$ or COOH is converted to the carboxylic acid chloride prior to being coupled to an amine compound as represented by formula 2. Equivalent amounts of the carboxylic acid chloride and the cephalosporin derivative (compound of formula 2) are reacted in an ether-water mixture in the presence of an acid acceptor such as sodium bicarbonate at about 0° C. for from 0.5 hour to about 2 hours. The coupled product is recovered by conventional methods.

Optionally, compounds of formula 1 wherein $R_4$ is other than hydrogen or a cation, $R_3$ is other than hydrogen or a cation or both $R_3$ and $R_4$ are other than hydrogen or a cation may be converted to compounds of formula 1 wherein $R_3$ and $R_4$ are both hydrogen by reacting the compounds of formula 1 ($R_3$ and $R_4$ are other than hydrogen or a cation) in trifluoroacetic acid at −10° C. to +10° C. for from 10 minutes to about 2 hours and recovering the desired compound therefrom.

The preferred compounds of this invention are those compounds of formula 1 wherein n is O, W is —$(CH_2)_{0-10}$— $CO_2R_4$ where $R_4$ is hydrogen or a straight or branched 1-4 carbon alkyl or —$SO_3H$, $R_2$ is a heterocyclicthio group as defined in formula 1, hydrogen, or acetyloxy, and $R_3$ is hydrogen.

The more preferred compounds are those compounds of formula 1 wherein n is O, W is —$(CH_2)_0$—$CO_2R_4$ where $R_4$ is hydrogen or a straight or branched 1-4 carbon alkyl group, $R_2$ is acetyloxy or heterocyclicthio group and $R_3$ is hydrogen.

The most preferred compounds of this invention are those compounds of formula 1 wherein n is O, W is —$(CH_2)_0$—$CH_2R_4$ and $R_4$ is hydrogen, $R_2$ is acetyloxy, 1-methyltetrazol-5-ylthio, 5-methyl-1,3,4-thiadiazol-2-ylthio and $R_3$ is hydrogen.

The acids as represented by formula 3 may be prepared by condensing 2-formylpyrrole with halogenated derivatives of carboxylic acids in a basic medium. For example, 2-formylpyrrole is reacted with bromoacetic acid in aqueous sodium hydroxide at room temperature to form (2-formyl-1-pyrryl)acetic acid.

The desirable halogenated (usually bromine or chlorine) carboxylic acids are either commercially available, may be prepared by means of the Hell-Volkard-Zelinsky (HVZ) reaction, or by means of the Hunsdiecher reaction employing the half-esters of dicarboxylic acids or by known methods.

Using the H-V-Z reaction,

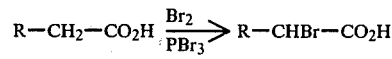

α-halogenated acids may be prepared wherein R can be an alkyl group, hydrogen, a —$(CH_2)p$—$CO_2$ Et group, p having the value as defined for formula 1.

The Hunsdiecker reaction may be employed to produce ω-halogenated carboxylic acids as shown

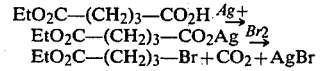

α-Sulfo-α-chloroacetic acid is prepared according to the general procedure described by LeBerre, *Bull Soc. Chem. Fr.*, 1973(1), 210–214. The diacid chloride of α-sulfo-α-chloroacetic acid is cautiously hydrolyzed in water-ether, followed by recovery of the α-sulfo-α-chloroacetic acid.

The halogenated acids thus produced may be condensed with 2-formylpyrrole as described above to give pyrryl substituted acetic acids.

Compounds of formula 2 wherein $R_1$ is hydrogen, $R_3$ is hydrogen or a cation and $R_2$ is hydrogen or acetyloxy are commercially available or may be prepared by methods well-known in the art. The corresponding compounds wherein $R_1$ is methoxy, $R_2$ is hydrogen or acetyloxy and $R_3$ is hydrogen may be prepared by the general procedures described in U.S. Pat. No. 3,778,432.

Compounds of formula 1 and 2 wherein n, W, $R_1$ and $R_2$ are as defined for formula 1 and $R_3$ is alkanoyloxymethyl may be prepared by reacting the corresponding acid in the form of a salt, such as, an alkali metal salt or the triethylammonium salt with a compound of the formula

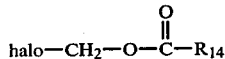

wherein halo is chlorine or bromine, and $R_{14}$ is a straight or branched alkyl group of from 1 to 4 carbon atoms, by the general procedure described in U.S. Pat. No. 3,655,658.

Compounds of formula 1 and 2 wherein n, W, $R_1$ and $R_2$ are as defined in formula 1 and $R_3$ is alkanoylaminomethyl or alkoxycarbonylaminomethyl are prepared by treating the sodium salt of acid derivatives of formula 1 or 2 in an organic solvent such a dimethylformamide or hexamethylphosphoramide at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of formula 1 and 2 wherein n, W, $R_1$ and $R_2$ are as defined in formula 1 and $R_3$ is p-(alkanoyloxy)benzyl are prepared by adding two equivalents of the p-(alkanoyloxy)benzyl alcohol to a suspension of sodium salts of acid derivatives of formula 1 or 2 and dimethylformamide or hexamethylphosphoramide after which the mixture is cooled to 0° C. 1.2 equivalents of dicyclohexylcarbodiimide and dimethylformamide are added dropwise to the mixture with stirring. The mixture is stirred at 0° C. for ½ to 3 hours and then an additional 2 to 5 hours at room temperature. The formed dicyclohexylurea is removed by filtration and the filtrate is diluted with chloroform, methylene chloride or ethylacetate, washed with water and dried to give the product.

Compounds of formula 1 and 2 wherein n, W, $R_1$ and $R_2$ are as defined in formula 1 and $R_3$ is aminoalkanoyloxymethyl are prepared by mixing a suspension of the sodium salt of an acid of formula 1 or 2 and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride, washed with water, aqueous base, then water. The organic phase is separated and the precipitate isolated by conventional means followed by deprotection of the amine group to give the product.

Compounds of formula 1 and 2 wherein $R_1$ is hydrogen or methoxy, $R_2$ is a heterocyclic thio group as described for compounds represented by formula 1 and $R_3$ is hydrogen are prepared by dissolving 1 equivalent of the acid, as represented by compounds of formula 1 and 2, in the form of a salt, such as the sodium salt, wherein $R_2$ is acetyloxy in about 500 to 2000 ml of water at a temperature of from about 30° to about 90° C. under a nitrogen atmosphere, and then adding 1 equivalent of a base, such as, sodium bicarbonate or triethylamine and 1 to 3 equivalents of the appropriate heterocyclic thiol selected from a compound having the following structure:

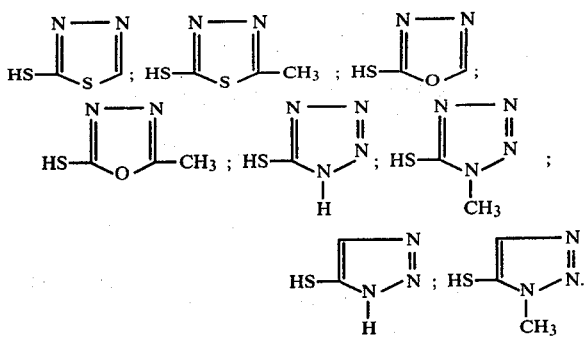

The mixture is stirred for from 2 to 6 hours at 30° C. to 90° C. and the desired compounds are recovered.

EXAMPLE 1

4-Bromobutanoic Acid

The mono silver salt of pentanedioic acid (0.05 m) is added to dry carbon tetrachloride to form a suspension. The suspension is heated to reflux and a slight excess of bromine (0.055 m based on the silver salt) in carbon tetrachloride is added to the refluxing suspension. Silver bromide is formed accompanied by the evolution of carbon dioxide. After the bromine color disappears, the silver bromide is removed by filtration. Carbon tetrachloride is removed in vacuo leaving a residue of the halogenated acid which is purified by distillation.

In like manner, substitution of the silver salt of butanedioic acid for silver pentanedioic acid gives the corresponding 3-bromopropanoic acid.

EXAMPLE 2

2-Bromohexanedioic acid, 6-ethyl ester

Using a modification of the procedure of Schwenk and Papa, J. Am. Chem. Soc., 70, 3626 (1948), 2-bromohexanedioic acid, 6-ethyl ester is prepared. The monoethyl ester of hexanedioic acid is added to an excess of thionyl chloride and the mixture is refluxed. Then a slight excess of bromine is added to the refluxing mixture. The bromine reacts quite rapidly as evidenced by the disappearance of the brown color. Removal of the thionyl chloride under vacuo and hydrolysis of the acid chloride yields the 2-bromohexanedioic acid, 6-ethyl ester which is used without further purification.

In like manner and using sufficient quantities of reactants such as the monoethyl esters of the following dicarboxylic acids: propanedioic acid, butanedioic acid, nonanedioic acid, decanedioic acid, undecanedioic acid and dodecanedioic acid in place of the monoethyl ester of hexanedioic acid gives respectively:
2-bromopropanedioic acid, 3-ethyl ester;
2-bromobutanedioic acid, 4-ethyl ester;
2-bromopentanedioic acid, 5-ethyl ester;
2-bromoheptanedioic acid, 7-ethyl ester;
2-bromooctanedioic acid, 8-ethyl ester;
2-bromononanedioic acid, 9-ethyl ester;
2-bromodecnedioic acid, 10-ethyl ester;
2-bromoundecanedioic acid, 11-ethyl ester; and
2-bromododecanedioic acid, 12-ethyl ester.

EXAMPLE 3

α-Sulfo-α-Chloroacetic Acid

The diacid chloride of α-sulfo-α-chloroacetic acid is prepared according to the procedure of LeBerre, *Bull Soc. Chem. Fr.*, 1973, (1) (Pt.2), 210–214. The diacid chloride is cautiously added to a stirred mixture of equal parts of water and ether. After the hydrolysis is complete, the phases are separated. The aqueous phase is extracted again with ether. The ether extracts are combined, dried over magnesium sulfate and then the ether is removed and the title compound is recovered.

EXAMPLE 4

(2-Formyl-1-pyrryl) acetic Acid

To an ice cold solution (about 0° C.) of sodium hydroxide (8.8 g in 30 ml of water) is added 9.5 g (0.1 m) of pyrrole-2-carboxaldehyde followed by the addition of bromoacetic acid (14 g, 0.11 m) in small portions. The solution is stirred at room temperature for 18 hours. Only a small trace of the pyrrole-2-carboxaldehyde could be detected by thin layer chromatography. The aqueous solution is first washed with chloroform, and then acidified to pH 3 with 6 N hydrochloric acid. The acidified solution is extracted with ethyl acetate which is dried over magnesium sulfate, filtered and flash evaporated. An oil is obtained which is crystallized from ethyl acetate-benzene to give 9.7 g of product (63%) yield) NMR(DMSO—$D_6$+$D_2O$)ppm(δ) 5.10(s,2); 6.3(q,1); 7.1(q,1); 7.25(m,1) and 9.58(s,1).

In a similar manner, when the halogenated alkanoic acids listed in Table 1 are substituted for bromoacetic acid and reacted with pyrrole-2-carboxaldehyde, the products listed in Table 1 are obtained.

TABLE 1

| Starting Carboxylic Acid | Pyrrole Derivative | Product |
|---|---|---|
| 3-Bromopropanoic acid | Pyrrole-2-carboxaldehyde | 3-(2-formyl-1-pyrryl)propanoic acid |
| 4-Bromobutanoic acid | Pyrrole-2-carboxaldehyde | 4-(2-formyl-1-pyrryl)butanoic acid |
| 2-Bromopropanoic acid | Pyrrole-2-carboxaldehyde | 2-(2-formyl-1-pyrryl)propanoic acid |
| 2-Bromobutanoic acid | Pyrrole-2-carboxaldehyde | 2-(2-formyl-1-pyrryl)butanoic acid |
| 2-Sulfo-2-chloroacetic acid | Pyrrole-2-carboxaldehyde | 2-sulfo-2-(2-formyl-1-pyrryl)acetic acid |
| 2-Bromopropanedioic acid, 3-ethyl ester | Pyrrole-2-carboxaldehyde | 2-(2-formyl-1-pyrryl)propanedioic acid, 3-ethyl ester |
| 2-Bromobutanedioic acid, 4-ethyl ester | Pyrrole-2-carboxaldehyde | 2-(2-formyl-1-pyrryl)butanedioic acid, 4-ethyl ester |
| 2-Bromopentanedioic acid, 5-ethyl ester | Pyrrole-2-carboxaldehyde | 2-(2-formyl-1-pyrryl)pentanedioic acid, 5-ethyl ester |
| 2-Bromohexanedioic acid, 6-ethyl ester | Pyrrole-2-carboxaldehyde | 2-(2-formyl-1-pyrryl)hexanedioic acid, 6-ethyl ester |
| 2-Bromoheptanedioic acid, 7-ethyl ester | Pyrrole-2-carboxaldehyde | 2-(2-formyl-1-pyrryl)heptanedioic acid, 7-ethyl ester |
| 2-Bromooctanedioic acid, 8-ethyl ester | Pyrrole-2-carboxaldehyde | 2-(2-formyl-1-pyrryl)octanedioic acid, 8-ethyl ester |
| 2-Bromononanedioic acid, 9-ethyl ester | Pyrrole-2-carboxaldehyde | 2-(2-formyl-1-pyrryl)nonanedioic acid, 9-ethyl ester |
| 2-Bromodecanedioic acid, 10-ethyl ester | Pyrrole-2-carboxaldehyde | 2-(2-formyl-1-pyrryl)decanedioic acid, 10-ethyl ester |
| 2-Bromoundecanedioic acid, 11-ethyl ester | Pyrrole-2-carboxaldehyde | 2-(2-formyl-1-pyrryl)undecanedioic acid, 11-ethyl ester |
| 2-Bromododecanedioc acid, 12-ethyl ester | Pyrrole-2-carboxaldehyde | 2-(2-formyl-1-pyrryl)dodecanedioic acid, 12-ethyl ester. |

EXAMPLE 5

3-[(Acetyloxy)methyl]-7-[[(2-formyl-1-pyrryl)acetyl]-amino]-8-oxo-5-thia-1-azabicyclo[4.2.0]oct-2-ene-carboxylic acid A solution of (2-formyl-1-pyrryl)acetic acid (3.06 g, 0.02 m) and triethylamine (2.8 ml; 0.02 m) in 80 ml of tetrahydrofuran (THF) is cooled to 0° C. While stirring, isobutyl chloroformate (2.6 ml, 0.02 m) is added and the temperature maintained at 0° C. for 15 minutes. A cold solution of 3-[(acetyloxy)methyl]-7-amino-8-oxo-5-thia-1-azabicyclo[4.2.0]oct-2-ene-2-carboxylic acid (5.44 g, 0.02 m) and triethylamine (2.8 ml, 0.02 m) in 72 ml of 50% aqueous THF is added to the previous solution with stirring.

The mixture is stirred at 5° C. for 1 hour and at room temperature for an additional hour. The THF is evaporated and the residue is dissolved in 100 ml of water and is washed with ethyl acetate. The aqueous phase is covered with a fresh layer of ethyl acetate, cooled in ice and acidified to pH 3 with 6 N hydrochloric acid. The mixture is filtered and the ethyl acetate separated. The aqueous phase is washed with fresh ethyl acetate. The combined ethyl acetate fractions are dried over magnesium sulfate, treated with charcoal, filtered and flash concentrated to 10–30 ml and added with vigorous stirring to a mixture of ether-hexane. The title compound precipitates and is recovered by filtration. The yield is 18%.

NMR(DMSO—D$_6$+D$_2$O)ppm($\delta$): 2.08(s,3); 3.6(broad s,2); 4.9(q,2); 5.1(m,3) 5.7(d,1); 6.3(q,1); 7.1(q,1); 7.3(m,1); and 9.56(s,1).

In like manner, 4-(2-formyl-1-pyrryl)butanoic acid, 2-sulfo-2-(2-formyl-1-pyrryl)acetic acid, 2-(2-formyl-1-pyrryl)propanedioic acid, 3-ethyl ester and 2-(2-formyl-1-pyrryl)octanedioic acid, 8-ethyl ester are substituted for (2-formyl-1-pyrryl)acetic acid and the following respective compounds are obtained:

3-[(acetyloxy)methyl]-7-[[4-(2-formyl-1-pyrryl)butyryl]amino]-8-oxo-5-thia-1-azabicyclo[4.2.0]oct-2-ene-2-carboxylic acid;

3-[(acetyloxy)methyl]-7-[[2-sulfo-2-(2-formyl-1-pyrryl)acetyl]amino]-8-oxo-5-thia-1-azabicyclo[4.2.0]oct-2-ene-2-carboxylic acid;

3-[(acetyloxy)methyl]-7-[[2-carboethoxy-2-(2-formyl-1-pyrryl)acetyl]amino]-8-oxo-5-thia-1-azabicyclo[4.2.0]-oct-2-ene-2-carboxylic acid; and 3-[(acetyloxy)methyl]-7-[[2-(5-carboethoxypentyl)-2-(2-formyl-1-pyrryl)acetyl]amino]-8-oxo-5-thia-1-azabicyclo-[4.2.0]oct-2-ene-2-carboxylic acid.

EXAMPLE 6

7-[[(2-Formyl-1-pyrryl)acetyl]amino]-3-[[(1-methyltetrazol-5-yl)thio]methyl]-8-oxo-5-thia-1-azabicyclo[4.2.0]oct-2-ene-carboxylic acid A solution of (2-formyl-1-pyrryl)acetic acid (3.06 g, 0.02 m) and triethylamine (2.8 ml, 0.02 m) in 80 ml of tetrahydrofuran (THF) is cooled to 0° C. While stirring, isobutyl chloroformate (2.6 ml, 0.02 m) is added and the temperature maintained at 0° C. for 15 minutes. A cold solution of 7-amino-3-[[(1-methyltetrazol-5-yl)thio]methyl]-8-oxo-5-thia-1-azabicyclo[4.2.0]oct-2-ene-2-carboxylic acid (6.16 g, 0.02 m) and triethylamine (2.8 ml, 0.02 m) in 72 ml of 50% aqueous THF is added to the previous solution with stirring.

The mixture is stirred at 5° C. for 1 hour and at room temperature for an additional hour. The THF is evaporated and the residue is dissolved in 100 ml of water and is washed with ethyl acetate. The aqueous phase is covered with a fresh layer of ethyl acetate, cooled in ice and acidified to pH 3 with 6 N hydrochloric acid. The mixture is filtered and the ethyl acetate separated. The aqueous phase is then extracted with fresh ethyl acetate. The combined ethyl acetate fractions are dried over magnesium sulfate, treated with charcoal, filtered and flash concentrated to 10–30 ml and then added with vigorous stirring to a mixture of ether-hexane. The title compound precipitates and is recovered by filtration. The yield is 35%.

NMR(DMSO—D$_6$+D$_2$O)ppm($\delta$) 3.73(broad s,2); 3.97(s,3); 4.35(broad s,2); 5.1(m,3); 5.87(d,1); 6.3(q,1); 7.08(q,1); 7.3(m,1) and 9.57(s,1).

In like manner and using the appropriate quantities of 7-amino-3-[[(5-methyl-1,3,4-thiadiazol-2-yl)thio]methyl]-8-oxo-5-thia-1-azabicyclo[4.2.0]oct-2-ene-2-carboxylic acid;

7-amino-3-[[(1,3,4-oxadiazol-2-yl)thio]methyl]-8-oxo-5-thia-1-azabicyclo[4.2.0]oct-2-ene-2-carboxylic acid;

7-amino-3-[[(5-methyl-1,3,4-oxadiazol-2-yl)thio]methyl]-8-oxo-5-thia-1-azabicyclo[4.2.0]oct-2-ene-2-carboxylic acid; and 7-amino-3-[[(1,2,3-triazol-5-yl)thio]methyl]-8-oxo-5-thia-1-azabicyclo[4.2.0]oct-2-ene-2-carboxylic acid in place of 7-amino-3-[[(1-methyltetrazol-5-yl)thio]methyl]-8-oxo-5-thia-1-azabicyclo[4.2.0]oct-2-ene-2-carboxylic acid, the following respective compounds are prepared:

7-[[(2-formyl-1-pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid;

7-[[(2-formyl-1-pyrryl)acetyl]amino]-3-[[(1,3,4-oxadiazol-2-yl)thio]methyl]-8-oxo-5-thia-1-azabicyclo[4.2.0]oct-2-ene-2-carboxylic acid;

7-[[(2-formyl-1-pyrryl)acetyl]amino]-3-[[(5-methyl-1,3,4-oxadiazol-2-yl)thio]methyl]-8-oxo-5-thia-1-azabicyclo[4.2.0]oct-2-ene-2-carboxylic acid; and 7-[[(2-formyl-1-pyrryl)acetyl]amino]-3-[[(1,2,3-triazol-5-yl)thio]methyl]-8-oxo-5-thia-1-azabicyclo[4.2.0]oct-2-ene-2-carboxylic acid.

EXAMPLE 7

3[(Acetyloxy)methyl]-7-[[(2-formyl-1-pyrryl)acetyl]amino]-8-oxo-5-thia-1-azabicyclo[4.2.0]oct-2-ene-2-carboxylic acid, tert-butyl ester 3-[(Acetyloxy)methyl]-7-amino-8-oxo-5-thia-1-azabicyclo[4.2.0]oct-2-ene-2-carboxylic acid, tert-butyl ester is prepared according to the procedure described in *J. Med. Chem.*, 9, 444 (1966).

A solution of (2-formyl-1-pyrryl)acetic acid (3.1 g, 0.02 m) in tetrahydrofuran (THF) is cooled to about 0° C. and 4.12 g (0.02 m) of dicyclohexylcarbodiimide is added in one portion with stirring for five minutes. Then 3-[(acetyloxy)methyl]-7-amino-8-oxo-5-thia-1-azabicyclo[4.2.0]oct-2-ene-2-carboxylic acid, tert-butyl ester (6.08 g, 0.02 m) in THF is added. The temperature is maintained at 0° C. for one hour and then the temperature is increased to 20° for about 18 hours and the solution filtered. The THF is removed at reduced pressure and the residue is taken up in ethyl acetate. The ethyl acetate is extracted with 1.0% aqueous sodium bicarbonate and water. The ethyl acetate is then filtered, dried and evaporated to give the title compound.

In like manner and using the proper quantities of 7-amino-3-[[(1,3,4-thiadiazol-2-yl)thio]methyl]-8-oxo-5-thia-1-azabicyclo[4.2.0]oct-2-ene-2-carboxylic acid, tert-butyl ester;

7-amino-3-[[(5-methyl-1,3,4-thiadiazol-2-yl)thio]methyl]-8-oxo-5-thia-1-azabicyclo[4.2.0]oct-2-ene-2-carboxylic acid, tert-butyl ester; and 7-amino-3-[[(1-methyltetrazol-5-yl)thio]methyl]-8-oxo-5-thia-1-azabicyclo[4.2.0]oct-2-ene-2-carboxylic acid, tert-butyl ester in place of 3-[(acetyloxy)methyl]-7-amino-8-oxo-5-thia-1-azabicyclo[4.2.0]oct-2-ene-2-carboxylic acid, tert-butyl ester, the following respective compounds are prepared:

7-[[(2-formyl-1-pyrryl)acetyl]amino]-3-[[(1,3,4-thiadiazol-2-yl)thio]methyl]-8-oxo-5-thia-1-azabicyclo[4.2.0]oct-2-ene-2-carboxylic acid, tert-butyl ester;

7-[[(2-formyl-1-pyrryl)acetyl]amino]-3-[[(5-methyl)-1,3,4-thiadiazol-2-yl)thio]methyl]-8-oxo-5-thia-1-azabicyclo[4.2.0]oct-2-ene-2-carboxylic acid, tert-butyl ester; and 7-[[(2-formyl-1-pyrryl)acetyl]amino]-3-[[(1-methyltetrazol-5-yl)thio]methyl]-8-oxo-5-thia-1-azabicyclo[4.2.0]oct-2-ene-2-carboxylic acid, tert-butyl ester.

EXAMPLE 8

3-[(Acetyloxy)methyl]-7-[[(2-formyl-1-pyrryl)acetyl]-amino]-8-oxo-5-thia-1-azabicyclo[4.2.0]oct-2-ene-2-carboxylic acid, 2-amino-3-methylbutyryloxy ester A suspension of 5 grams of 3-[(acetyloxy)methyl]-7-[[(2-formyl-1-pyrryl)acetyl]amino]-8-oxo-5-thia-1-azabicyclo[4.2.0]oct-2-ene-2-carboxylic acid sodium salt and 8.5 grams of N-tert-butoxycarbonyl-L-valine chloromethyl ester, prepared according to the general procedure described in W. German Offen. No. 2,236,620, are mixed in 100 ml of dimethylformamide (DMF) and stirred for 72 hours. The mixture is diluted with ethyl acetate, washed with water and aqueous sodium bicarbonate and again with water. The ethyl acetate portion is dried over magnesium sulfate, filtered and evaporated to dryness to give 3-[(acetyloxy)methyl]-7-[[(2-formyl-1-pyrryl)acetyl]amino]-8-oxo-5-thia-1-azabicyclo[4.2.0]oct-2-ene-2-carboxylic acid N-tert-butoxycarbonyl-2-amino-3-methylbutyryloxymethyl ester from which the protecting group can be removed by standard procedures to give the title compound.

EXAMPLE 9

7-[[(2-Formyl-1-pyrryl)acetyl]amino]-3-[[(1-methyltetrazol-5-yl)thio]methyl]-8-oxo-5-thia-1-azabicyclo[4.2.0]oct-2-ene-2-carboxylic acid acetyloxymethyl ester The sodium salt of 7-[[(2-formyl-1-pyrryl)acetyl]-amino]-3-[[(1-methyltetrazol-5-yl)thio]methyl]-8-oxo-5-thia-1-azabicyclo[4.2.0]oct-2-ene-2-carboxylic acid, 3 grams, is added to about 40 ml of dry dimethylformamide (DMF) and stirred for 30 minutes. The 4.0 ml of chloromethyl acetate in 5 ml of DMF was added. This mixture is stirred for about 4 hours at room temperature. This mixture is diluted with ethyl acetate and thoroughly washed with water. The ethyl acetate portion is dried over sodium sulfate, filtered and evaporated to give the title compound.

In like manner and using sufficient quantities of chloromethyl propionate, chloromethyl butyrate and chloromethyl pivalate in place of chloromethyl acetate, the following representative compounds are prepared:

7-[[(2-formyl-1-pyrryl)acetyl]amino]-3-[[(1-methyltetrazol-5-yl)thio]methyl]-8-oxo-5-thia-1-azabicyclo[4.2.0]oct-2-ene-2-carboxylic acid propionyloxymethyl ester;

7-[[(2-formyl-1-pyrryl)acetyl]amino]-3-[[(1-methyltetrazol-5-yl)thio]methyl]-8-oxo-5-thia-1-azabicyclo[4.2.0]oct-2-ene-2-carboxylic acid butyryloxymethyl ester; and 7-[[(2-formyl-1-pyrryl)acetyl]amino]-3-[[(1-methyltetrazol-5-yl)thio]methyl]-8-oxo-5-thia-1-azabicyclo[4.2.0]oct-2-ene-2-carboxylic acid pivaloyloxymethyl ester.

EXAMPLE 10

3-[(Acetyloxy)methyl]-7-[[2-carboethoxy-2-(2-formyl-1-pyrryl)acetyl]amino]-8-oxo-5-thia-1-azabicyclo[4.2.0]oct-2-ene-2-carboxylic acid p-pivaloyloxybenzyl ester 3-[(Acetyloxy)methyl]-7-[[(2-carboethoxy-2-(2-formyl-1-pyrryl)acetyl]amino]-8-oxo-5-thia-1-azabicyclo[4.2.0]oct-2-ene-2-carboxylic acid sodium salt, 6.6 mmole, is added to 25 ml of dimethylformamide (DMF) with stirring. Then 2 equivalents of p-(pivaloyloxy)benzyl alcohol is added and the mixture cooled to 0° C. To this mixture is added 7.2 mmole of dicyclohexylcarbodiimide in 7.5 ml of DMF. Stirring is continued at 0° C. for 1 hour and for an additional hour at room temperature. Filtration removes dicyclohexylurea formed in the reaction. The reaction mixture is diluted with ethyl acetate, washed thoroughly with water and the organic phase is dried and filtered. Evaporation of the ethyl acetate gives the title compound.

In like manner, substituting sufficient quantities of p-(acetyloxy)benzyl alcohol, p-(propionyloxy)benzyl alcohol, and p-(valeryloxy)benzyl alcohol, for p-(pivaloyloxy)benzyl alcohol, the respective compounds are produced:

3-[(acetyloxy)methyl]-7-[[2-carboethoxy-2-(2-formyl-1-pyrryl)acetyl]amino]-8-oxo-5-thia-1-azabicyclo[4.2.0]oct-2-ene-2-carboxylic acid p-(acetyloxy)benzyl ester;

3-[(acetyloxy)methyl]-7-[[2-carboethoxy-2-(formyl-1-pyrryl)acetyl]amino]-8-oxo-5-thia-1-azabicyclo[4.2.0]oct-2-ene-2-carboxylic acid p-(propionyloxy)benzyl ester; and 3-[(acetyloxy)methyl]-7-[[2-carboethoxy-2-(2-formyl-1-pyrryl)acetyl]amino]-8-oxo-5-thia-1-azabicyclo[4.2.0]oct-2-ene-2-carboxylic acid p-(valeryloxy)benzyl ester.

EXAMPLE 11

3-[(Acetyloxy)methyl]-7-[[(2-formyl-1-pyrryl)acetyl]-amino]-8-oxo-5-thia-1-azabicyclo[4.2.0]oct-2-ene-2-carboxylic acid N-ethoxycarbonyl-N-methylaminomethyl ester The sodium salt of 3-[(acetyloxy)methyl]-7-[[(2-formyl-1-pyrryl)acetyl]amino]-8-oxo-5-thia-1-azabicyclo[4.2.0]oct-2-ene-2-carboxylic acid (2.5 mmole) in 50 ml of dimethylformamide (DMF) is treated at room temperature with 2.5 mmole of N-chloromethyl-N-methylurethane for 1 hour. The mixture is carefully poured into ice water and the precipitated solid is removed by filtration and is then washed with water. The filtered solid is dissolved in ethyl acetate and washed with aqueous sodium bicarbonate and then with water. The organic layer is dried over magnesium sulfate, filtered and evaporated to dryness to give the title compound.

In like manner and using sufficient quantities of N-methyl-N-propionylaminomethyl chloride or N-acetylaminomethyl chloride for N-chloromethyl urethane the following respective compounds are obtained:

3-[(acetyloxy)methyl]-7-[[(2-formyl-1-pyrryl)acetyl]-amino]-8-oxo-5-thia-1-azabicyclo[4.2.0]oct-2-ene-2-carboxylic acid N-methyl-N-propionylaminomethyl ester; and 3[(acetyloxy)methyl]-7-[[(2-formyl-1-pyrryl)acetyl]-amino]-8-oxo-5-thia-1-azabicyclo[4.2.0]oct-2-ene-2-carboxylic acid N-acetylaminomethyl ester.

EXAMPLE 12

3-[(Acetyloxy)methyl]-7-[[(2-formyl-1-pyrryl)acetyl]-amino]-7-methoxy-8-oxo-5-thia-1-azabicyclo[4.2.0]oct-2-ene-2-carboxylic acid A solution of (2-formyl-1-pyrryl)acetic acid (3.06 g, 0.02 m) and triethylamine (2.8 ml; 0.02 m) in 80 ml of tetrahydrofuran (THF) is cooled to 0° C. While stirring, isobutyl chloroformate (2.6 ml, 0.02 m) is added and the temperature maintained at 0° C. for 15 minutes. A cold solution of 3-[(acetyloxy)methyl]-7-amino-7-methoxy-8-oxo-5-thia-1-azabicyclo[4.2.0]oct-2-ene-2-carboxylic acid (5.44 g, 0.02 m) and triethylamine (2.8 ml, 0.02 m)

in 72 ml of 50% aqueous THF is added to the previous solution with stirring.

The mixture is stirred at 5° C. for 1 hour and at room temperature for an additional hour. The THF is evaporated and the residue is dissolved in 100 ml of water and is washed with ethyl acetate. The aqueous phase is covered with a fresh layer of ethyl acetate, cooled in ice and acidified to pH 3 with 6 N hydrochloric acid. The mixture is filtered and the ethyl acetate separated. The aqueous phase is washed with fresh ethyl acetate. The combined ethyl acetate fractions are dried over magnesium sulfate, treated with charcoal, filtered and flash concentrated to 10-30 ml and added with vigorous stirring to a mixture of ether-hexane. The title compound precipitates and is recovered by filtration.

In like manner substituting 2-(2-formyl-1-pyrryl)-propanoic acid, and 2-(2-formyl-1-pyrryl)heptanedioic acid, 7-ethyl ester for 2-(formyl-1-pyrryl)acetic acid the following respective compounds are obtained:

3-[(acetyloxy)methyl]-7-[[2-methyl-2-(2-formyl-1-pyrryl)acetyl]amino]-7-methoxy-8-oxo-5-thia-1-azabicyclo[4.2.0]oct-2-ene-2-carboxylic acid; and 3-[(acetyloxy)methyl]-7-[[2-(4-carboethoxybutyl)-2-(2-formyl-1-pyrryl)acetyl]amino]-7-methoxy-8-oxo-5-thia-1-azabicyclo[4.2.0]oct-2-ene-2-carboxylic acid.

EXAMPLE 13

7-[[(2-Formyl-1-pyrryl)acetyl]amino]-3-[[(1-methyltetrazol-5-yl)thio]methyl]-8-oxo-5-thia-1-azabicyclo[4.2.0]oct-2-ene-2-carboxylic acid 3-[(Acetyloxy)methyl]-7-[[(2-formyl-1-pyrryl)acetyl]-amino]-8-oxo-5-thia-1-azabicyclo[4.2.0]oct-2-ene-2-carboxylic acid, sodium salt, 0.01 mole, is dissolved in water containing 0.01 mole of sodium bicarbonate. This mixture is heated to about 60° C. and 0.015 mole of (1-methyltetrazol-5-yl)thiol is added. The reaction mixture is stirred for 6 hours at 60° C. The reaction mixture is cooled to about 25° C. and the pH adjusted to 2.0 with 6 N HCl. The acidified mixture is extracted with ethyl acetate. The ethyl acetate is dried over magnesium sulfate and evaporated under reduced pressure to give the title compound.

In like manner and using the appropriate amounts of tetrazol-5-ylthiol, 1,3,4-thiadiazol-2-ylthiol and 5-methyl-1,3,4-thiadiazol-2-ylthiol in place of 1-methyltetrazol-5-ylthiol the following respective cephalosporins are obtained:

7-[[(2-Formyl-1-pyrryl)acetyl]amino]-3-[[(tetrazol-5-yl)thio]methyl]-8-oxo-5-thia-1-azabicyclo[4.2.0]oct-2-ene-2-carboxylic acid;

7-[[(2-formyl-1-pyrryl)acetyl]amino]-3-[[(1,3,4-thiadiazol-2-yl)thio]methyl]-8-oxo-5-thia-1-azabicyclo[4.2.0]oct-2-ene-2-carboxylic acid; and 7-[[(2-formyl-1-pyrryl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid.

EXAMPLE 14

3-[(Acetyloxy)methyl]-7-[[2-sulfo-2-(2-formyl-1-pyrryl)acetyl]amino]-8-oxo-5-thia-1-azabicyclo[4.2.0]oct-2-ene-2-carboxylic acid 2-Sulfo-2-(2-formyl-1-pyrryl)acetic acid (0.01 m) is treated with excess thionyl chloride in ether at room temperature according to the general procedure in *J. Med. Chem.*, 15, 1105 (1972) until the evolution of gas stops. Dimethylformamide is added and the solution is warmed to about 30° C. for 1 hour. Additional ether is added, followed by hexane and the solution is cooled to about −25° C. 2-Sulfo-2-(2-formyl-1-pyrryl)acetyl chloride is recovered from the mixture.

A solution of 2-sulfo-2-(2-formyl-1-pyrryl)acetyl chloride (0.01 m) in ether is added to 3-[(acetyloxy)methyl]-7-amino-8-oxo-5-thia-1-azabicyclo[4.2.0]oct-2-ene-2-carboxylic acid (0.01 m) and sodium bicarbonate (0.03 m) in water. After 30 minutes the phases are separated, the pH adjusted to about 6.5 and the aqueous extracted with ethyl acetate. The ethyl acetate is separated from the aqueous phase, dried over magnesium sulfate and flash evaporated to give the title compound.

EXAMPLE 15

7-[[(2-Formyl-1-pyrryl)acetyl]amino]-7-methoxy-3-methyl-8-oxo-5-thia-1-azabicyclo[4.2.0]oct-2-ene-2-carboxylic acid A solution of (2-formyl-1-pyrryl)acetic acid (0.02 m) and triethylamine (0.02 ml) in tetrahydrofuran (THF) is cooled to 0° C. While stirring, isobutyl chloroformate (0.02 m) is added and the temperature is maintained at 0° C. for 15 minutes. A cold solution of 7-amino-3-methyl-8-oxo-5-thia-1-azabicyclo[4.2.0]oct-2-ene-2-carboxylic acid (0.02 m) and triethylamine (0.02 m) in 50% aqueous THF is added to the previous solution with stirring.

The mixture is stirred at 5° C. for 1 hour, and at room temperature for 1 hour. The THF is evaporated and the residue dissolved in 100 ml of water which is extracted with ethyl acetate. The phases are separated, the aqueous phase is layered with additional ethyl acetate, and cooled in an ice bath. The aqueous phase is acidified to a pH of 3 with hydrochloric acid. This mixture is filtered and the phases separated. The combined ethyl acetate extracts are dried over magnesium sulfate, treated with charcoal, filtered and flash concentrated. The residue is added to a cold mixture of ether-hexane. The title compound precipitates and is recovered by filtration.

EXAMPLE 16

3-[(Acetyloxy)methyl]-7-[[2-carboxy-2-(2-formyl-1-pyrryl)acetyl]amino]-8-oxo-5-thia-1-azabicyclo[4.2.0]oct-2-ene-2-carboxylic acid 3-[(Acetyloxy)methyl]-7-[[2-carboethoxy-2-(2-formyl-1-pyrryl)acetyl]amino]-8-oxo-5-thia-1-azabicyclo[4.2.0]oct-2-ene-2-carboxylic acid, tert-butyl ester, 0.05 m, is added to 50 ml of trifluoroacetic acid which is maintained at 0° C. The reaction mixture is stirred at 0° C. for 15 minutes and then at 10° C. for 15 minutes. The trifluoroacetic acid is removed in vacuo, the temperature of the mixture not rising above 20° C. The residue was taken up in methanol-water (4:1) and the pH adjusted to about 4 with ammonium hydroxide. The precipitate is filtered and the filtrate is concentrated and cooled to give the title compound.

The daily dosage of the active ingredient may range from 1 mg of about 500 mg. The exact amount will vary with the patients size, age and type of infection.

| A typical tablet can have the following composition | |
|---|---|
| 3-[(Acetyloxy)methyl]-7-[[2-carboxy-2-(2-formyl-1-pyrryl)-acetyl]amino]-8-oxo-5-thia-1-azabicyclo[4.2.0]oct-2-ene-2-carboxylic acid. | 50 mg |
| Lactose, USP | 250 mg |
| Cornstarch, USP | 50 mg |
| Cornstarch, USP (as 10% starch paste) | 5 mg |

| -continued | |
|---|---|
| A typical tablet can have the following composition | |
| Calcium Stearate | 2 mg |

Suitable size tablets can be prepared using a 5/16 inch diameter standard concave punch.

| A typical ointment can have the following composition | |
|---|---|
| 3-[(Acetyloxy)methyl]-7-[[2-carboxy-2-(2-formyl-1-pyrryl)-acetyl]amino]-8-oxo-5-thia-1-azabicyclo[4.2.0]oct-2-ene-2-carboxylic acid. | · 50 mg/grams of ointment |
| Hydrophilic Base | |
| Cetyl alcohol | 15% |
| White wax | 1% |
| Sodium Lauryl sulfate | 2% |
| Propylene glycol | 10% |
| Water | 72% |

Add the cephalosporin derivative to a small amount of water and incorporate into the base.

| A typical parenteral solution may have the following composition | |
|---|---|
| 3-[(Acetyloxy)methyl]-7-[[2-carboxy-2-(2-formyl-1-pyrryl)-acetyl]amino]-8-oxo-5-thia-1-azabicyclo[4.2.0]oct-2-ene- | |
| 2-carboxylic acid | 1.0 g |
| White beeswax | 1.0 g |
| Peanut oil, to make | 10.0 cc |

Melt wax into a portion of the peanut oil and then add the remaining oil to the mix. Sterilize the mix at 150° C. for 2 hours with dry heat. Under sterile conditions mix the cephalosporin into the wax-oil mixture and place in an ampul and seal said ampul. For use, dilute contents of ampul with 10 cc of pure water. Each cc contains 50 mg of cephalosporin.

We claim:

1. A compound selected from the base of the formula

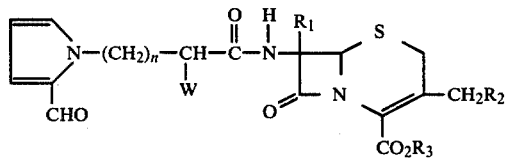

wherein n is 0, 1, 2 or 3; W is hydrogen, a straight or branched alkyl group of from 1 to 4 carbon atoms, a sulfonic acid group, or a —$(CH_2)_p$—$CO_2R_4$ group wherein p has a value of 0 or an integer of from 1 to 10 and $R_4$ is hydrogen, a pharmaceutically acceptable non-toxic cation selected from the alkali metal group, the alkaline earth metal group, ammonium, or organic ammonium compounds derived from a primary, a secondary or a tertiary amine, a straight or branched alkyl group of from 1 to 4 carbon atoms; $R_1$ is hydrogen or methoxy; $R_2$ is hydrogen or alkanoyloxy in which the alkanoyl group contains from 2 to 5 carbon atoms; $R_3$ is hydrogen, a pharmaceutically acceptable non-toxic cation; a straight or branched alkyl group of from 1 to 4 carbon atoms, an alkanoyloxymethyl group in which the alkanoyl portion is straight or branched and has from 2 to 5 carbon atoms, an alkanoylaminomethyl group in which the alkanoyl portion is straight or branched and has from 2 to 5 carbon atoms and the amine nitrogen may be substituted with a straight or branched alkyl group having 1 to 4 carbon atoms, an alkoxycarbonylaminomethyl group in which the alkoxy portion is straight or branched and has from 1 to 4 carbon atoms and the amine nitrogen may be substituted with a straight or branched alkyl group of from 1 to 4 carbon atoms, p-(alkanoyloxy)benzyl groups in which the alkanoyl portion is straight or branched and has from 2 to 5 carbon atoms, an aminoalkanoyloxymethyl group in which the alkanoyl portion has from 2 to 15 carbon atoms and the amino nitrogen may be mono- or di-substituted with a straight or branched alkyl group having from 1 to 4 carbon atoms; with the proviso that when $R_3$ is other than hydrogen or a cation and W is —$(CH_2)_p$—$CO_2R_4$ with p being from 1 to 10, then $R_4$ is other than hydrogen or a cation; and pharmaceutically acceptable salts thereof.

2. A compound according to claim 1 wherein $R_1$ is hydrogen.

3. A compound according to claim 2 wherein $R_3$ is hydrogen.

4. A compound according to claim 3 wherein $R_2$ is hydrogen.

5. A compound according to claim 3 wherein $R_2$ is an alkanoyloxy group containing from 2 to 5 carbon atoms.

6. A compound selected from the base of the formula

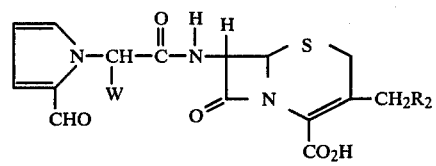

wherein W is hydrogen, a straight or branched alkyl group of from 1 to 4 carbon atoms, a sulfonic acid group or a —$(CH_2)_p$—$CO_2R_4$ group wherein p is 0 or an integer of from 1 to 10 and $R_4$ is hydrogen, a pharmaceutically acceptable non-toxic cation selected from the alkali metal or the alkaline earth metal groups, ammonium, organic ammonium compounds derived from a primary, a second or a tertiary amine, or a straight or branched alkyl group of from 1 to 4 carbon atoms and $R_2$ is hydrogen or alkanoyloxy in which the alkanoyl group contains from 2 to 5 carbon atoms; $R_3$ is hydrogen, a pharmaceutically acceptable non-toxic anion or cation charge; a straight or branched alkyl group of from 1 to 4 carbon atoms, an alkanoyloxymethyl group in which the alkanoyl portion is straight or branched and has from 2 to 5 carbon atoms, an alkanoylaminomethyl group in which the alkanoyl portion is straight or branched and has from 2 to 5 carbon atoms and the amine nitrogen may be substituted with a straight or branched alkyl group having 1 to 4 carbon atoms, an alkoxycarbonylaminomethyl group in which the alkoxy portion is straight or branched and has from 1 to 4 carbon atoms and the amine nitrogen may be substituted with a straight or branched alkyl group of from 1 to 4 carbon atoms, p-(alkanoyloxy)benzyl groups in which the alkanoyl portion is straight or branched and has from 2 to 5 carbon atoms, an aminoalkanoyloxymethyl group in which the alkanoyl portion has from 2 to 15 carbon atoms and the amino nitrogen may be mono- or di-substituted with a straight or branched alkyl group having from 1 to 4 carbon atoms; with the proviso that when $R_3$ is other than hydrogen or a cation and W is —$(CH_2)_p CO_2 R_4$ with p being from 1 to 10, then $R_4$ is other than hydrogen or a cation; and pharmaceutically acceptable salts thereof.

7. A compound according to claim 6 wherein W is hydrogen or a —$(CH_2)_p$—$CO_2 R_4$ group in which p is zero and $R_4$ is hydrogen.

8. A compound according to claim 7 wherein $R_2$ is acetyloxy.

9. A compound according to claim 8 which is 3-[(acetyloxy)methyl]-7-[[(2-formyl-1-pyrryl)acetyl]amino]-8-oxo-5-thia-1-azabicyclo[4.2.0]oct-2-ene-2-carboxylic acid or a pharmaceutically acceptable salt thereof.

10. A compound according to claim 8 which is 3-[(acetyloxy)methyl]-7-[[2-carboxy-2-(2-formyl-1-pyrryl)acetyl]amino]-8-oxo-5-thia-1-azabicyclo[4.2.0]-oct-2-ene-2-carboxylic acid or a pharmaceutically acceptable salt thereof.

11. A compound according to claim 6 wherein W is a sulfonic acid group.

12. A compound according to claim 11 which is 3-[(acetyloxy)methyl]-7-[[2-sulfo-2-(2-formyl-1-pyrryl)acetyl]amino]-8-oxo-5-thia-1-azabicyclo[4.2.0]oct-2-ene-2-carboxylic acid or a pharmaceutically acceptable salt thereof.

* * * * *